(12) United States Patent
Schenkl et al.

(10) Patent No.: US 8,531,670 B2
(45) Date of Patent: *Sep. 10, 2013

(54) OPTICAL SENSOR, IN PARTICULAR FOR INSTALLATION IN A HOUSEHOLD WASHING MACHINE OR DISHWASHER

(75) Inventors: Johann Schenkl, Bodenwoehr (DE); Martin Brabec, Nabburg (DE); Thomas Hanauer, Nabburg (DE)

(73) Assignee: emz-Hanauer GmbH & Co. KGaA, Nabburg (DE)

( * ) Notice: Subject to any disclaimer, the term of this patent is extended or adjusted under 35 U.S.C. 154(b) by 125 days.

This patent is subject to a terminal disclaimer.

(21) Appl. No.: 13/172,926

(22) Filed: Jun. 30, 2011

(65) Prior Publication Data

US 2012/0162652 A1    Jun. 28, 2012

(30) Foreign Application Priority Data

Jul. 5, 2010    (DE) .......................... 10 2010 026 068

(51) Int. Cl.
*G01N 21/59*    (2006.01)

(52) U.S. Cl.
USPC .......................... 356/436; 356/432; 250/574

(58) Field of Classification Search
USPC .................. 356/432–437, 39, 410; 250/343, 250/341, 574
See application file for complete search history.

(56) References Cited

U.S. PATENT DOCUMENTS 4,227,814 A * 10/1980 Soodak et al. ................ 356/410
4,427,293 A *  1/1984 Harmer ......................... 356/133
4,440,022 A *  4/1984 Masom .......................... 73/293
(Continued)

FOREIGN PATENT DOCUMENTS

DE    2654726 B1    3/1978
DE    3339348 A1    6/1989
(Continued)

OTHER PUBLICATIONS

Office Action from State Intellectual Property Office of People's Republic of China with English translation issued Jan. 29, 2013 for co-pending CN Appl. No. 201110186541.1 for Optical sensor, in particular for installation in a household washing machine or dishwasher.

*Primary Examiner* — Sang Nguyen
(74) *Attorney, Agent, or Firm* — Robert R. Deleault, Esq.; Mesmer & Deleault, PLLC

(57) ABSTRACT

An optical sensor to measure the turbidity of wash water in a household washing machine or dishwasher, includes a housing having a housing interior containing a measurement module having a light-emitting element and a light-receiving element, the measurement module defining a measurement light path which extends from the light-emitting element to the light-receiving element and passes outside the housing over a part of its path length. The light-emitting element and the light-receiving element are arranged together in a first subspace of the housing interior, and the measurement light path extends over a part of its path length through at least one second subspace of the housing interior, which is sealed from the first subspace. All the electrical/electronic components of the measurement module are fitted in the first subspace, so that any ingress of wash water into the second subspace does not compromise the electrical functionality of the sensor.

20 Claims, 2 Drawing Sheets

(56) References Cited

U.S. PATENT DOCUMENTS

| | | | |
|---|---|---|---|
| 4,929,929 A | 5/1990 | Romer | |
| 5,009,064 A | 4/1991 | Grob et al. | |
| 5,680,111 A * | 10/1997 | Danby et al. | 340/632 |
| 5,946,084 A * | 8/1999 | Kubulins | 356/128 |
| 5,987,351 A | 11/1999 | Chance | |
| 6,510,330 B1 * | 1/2003 | Enejder | 600/322 |
| 7,230,687 B2 * | 6/2007 | O'Mahony et al. | 356/39 |
| 2009/0140754 A1 | 6/2009 | Schenkl et al. | |
| 2010/0027015 A1 | 2/2010 | Schweng et al. | |
| 2012/0001099 A1 * | 1/2012 | Schenkl et al. | 250/574 |

FOREIGN PATENT DOCUMENTS

| | | |
|---|---|---|
| DE | 3818416 C1 | 9/1989 |
| DE | 10133970 A1 | 2/2003 |
| DE | 10314923 A1 | 11/2004 |
| DE | 10344111 A1 | 5/2005 |
| DE | 102008050109 A1 | 1/2010 |
| EP | 0597566 A1 | 5/1994 |
| GB | 1598333 | 5/1981 |
| WO | 9116618 A1 | 10/1991 |
| WO | 2006050767 A2 | 5/2006 |

* cited by examiner

OPTICAL SENSOR, IN PARTICULAR FOR INSTALLATION IN A HOUSEHOLD WASHING MACHINE OR DISHWASHER

BACKGROUND OF THE INVENTION

1. Field of the Invention

The present invention relates generally to an optical sensor, in particular for installation in a household washing machine or dishwasher.

2. Description of the Prior Art

An optical sensor used for installation in a household washing machine or dishwasher comprises a housing having a housing interior and, arranged in the housing interior, a measurement module having a light-emitting element and a light-receiving element, the measurement module defining a measurement light path which extends from the light-emitting element to the light-receiving element and passes outside the housing over a part of its path length.

An optical sensor having such a configuration is presented, for example, in WO 2006/050767 A2, see particularly FIGS. 1 to 4 therein.

Optical sensors of this type can be used in particular as turbidity sensors with which the turbidity of the wash water can be determined in a washing machine or a dishwasher. From the turbidity, it is possible to draw conclusions about the degree of soiling of the laundry to be cleaned or the kitchenware to be cleaned. In order to be able to measure the turbidity of the wash water, the path segment of the measurement light path lying outside the housing extends through a wash compartment of the relevant machine, which is flushed with the wash water. For example, to this end the sensor is installed in an assembly opening of a wall of the machine, delimiting the wash compartment, in such a way that it partially projects into the wash compartment, the light travelling along the measurement light path emerging from the housing at a first point inside the wash compartment and re-entering the housing at a second point, and the light experiencing an attenuation dependent on the turbidity of the wash water on the path segment of the measurement light path lying between the two housing points.

The term wash water is used here generically for any washing liquids which are used to clean the laundry or the kitchenware. Besides water, the washing liquid generally also contains various additives, in particular cleaning substances, but also conditioners or other assisting substances.

SUMMARY OF THE INVENTION

It is an object with optical sensors of the type considered here to ensure reliable protection against the entry of wash water into those sensor regions which contain the electrical/electronic components of the sensor, including the light-emitting element and the light-receiving element.

In order to achieve this object, the present invention proposes that the light-emitting element and the light-receiving element be arranged together in a first subspace of the housing interior, and that the measurement light path extend over a part of its path length through at least one second subspace of the housing interior, which is sealed from the first subspace. Preferably, all the electrical/electronic components of the measurement module are fitted in the first subspace, for instance evaluation electronics arranged on a common printed circuit board with the light-emitting element and the light-receiving element. The effect achieved by sealing the first subspace with respect to the at least one second subspace is that any entry of wash water into the second subspace does not lead to interference with or even failure of the electrical function of the sensor. Furthermore, the electrical protection of the machine per se can be improved, for example when the sensor is run on a mains voltage which could lead to dangerous short circuits in the event of water entering the first subspace.

The at least one second subspace is expediently formed in a housing region which is intended to be immersed in a space which is flushed with liquid. For optimal protection of the components of the measurement module which are fitted in the first subspace, the first subspace is preferably delimited only by such wall parts of the housing as are free from a liquid environment when the optical sensor is installed as intended. This prevents wash water outside the housing from being able to enter the first subspace via the sealing point between the first and second subspaces, for example as a result of a housing perforation inadvertently introduced during assembly or in use.

In a preferred configuration, the measurement module comprises at least one light guide body made of transparent material, which guides the light along a part of the measurement light path. The light guide body comprises an entry point opening into the first subspace for a light beam coming from the light-emitting element and/or an exit point opening into the first subspace for a light beam directed at the light-receiving element. It furthermore projects into the at least one second subspace. The at least one light guide body preferably has two reflection surfaces, which are used for total reflection of the light guided along the measurement light path. A light beam directed from the light-emitting element onto the entry point of the at least one light guide body in this case travels inside the at least one light guide body to a first of the two reflection surfaces, where it is totally reflected in the direction of the second reflection surface, the path segment of the measurement light path lying outside the housing being situated between the two reflection surfaces. At the second reflection surface, the light beam is totally reflected again and is then guided inside the at least one light guide body to the exit point, from which it travels to the light-receiving element.

In order to seal the first subspace from the at least one second subspace, the light guide body may be sealed with respect to the housing. In order to seal the light guide body with respect to the housing, a separate sealing element may for example be provided which is fitted between the light guide body and the housing. It is to be understood that instead of a separate sealing element, a sealing element produced integrally with the light guide body may for example be provided. Conventional two-component injection moulding techniques readily make it possible to produce a light guide body having a sealing element, which is formed integrally thereon and may optionally consist of a softer material than the light guide body. It is moreover also conceivable to achieve the desired sealing between the light guide body and the housing by adhesively bonding the light guide body into the housing, with the bonding site ensuring the requested leaktightness/leakproofness. It is furthermore conceivable to achieve the desired leaktightness/leakproofness by a press fit of the light guide body in the housing or by a welded connection.

According to a refinement, the housing has a cup-shaped main housing body with a cup shell and a cup bottom formed with a plurality of extensions, the light guide body having a base part and two projections integrally connected to the base part and each projecting into one of the extensions. In order to seal the first subspace from the at least one second subspace, the base part of the light guide body may be sealed with respect to the cup shell of the main housing body. To this end, it is recommendable for the base part of the light guide body to fill the inner cross section of the cup shell essentially fully. For example, the base part of the light guide body may have a circular contour and be seated in a correspondingly cylindrical region of the cup shell.

As an alternative to installing the at least one light guide body so that it is sealed with respect to the housing, it is conceivable to provide a partition membrane which is separate from the light guide body, is transparent to the measurement light, extends transversely through the housing interior and separates the first subspace in a leak-tight/leak-proof fashion from the at least one second subspace.

The present invention will be further explained below with the aid of the appended drawings.

DETAILED DESCRIPTION OF THE PREFERRED EMBODIMENT

Figure 1:
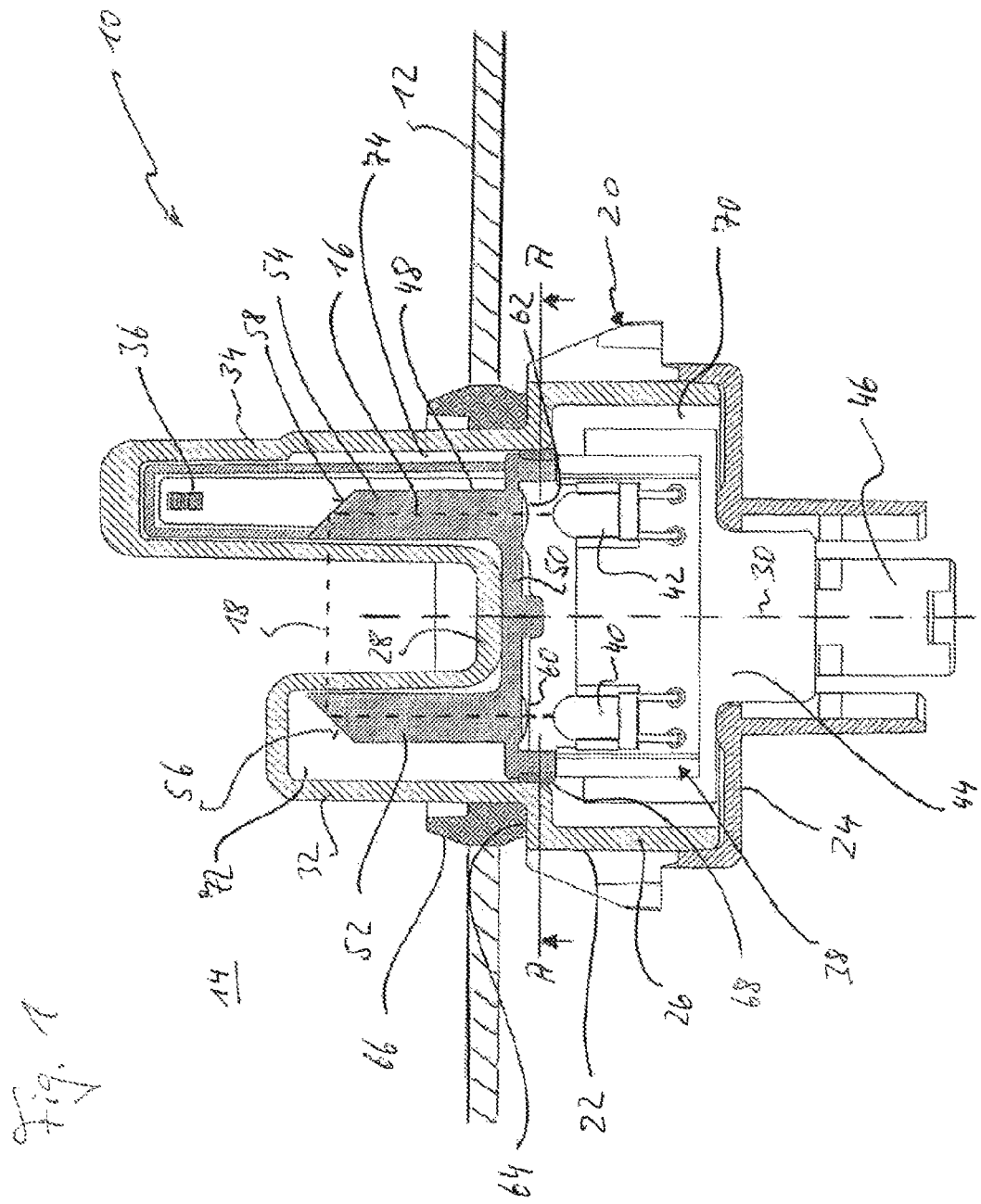
FIG. 1 shows an axial longitudinal section through an optical sensor according to an exemplary embodiment.
Figure 2:
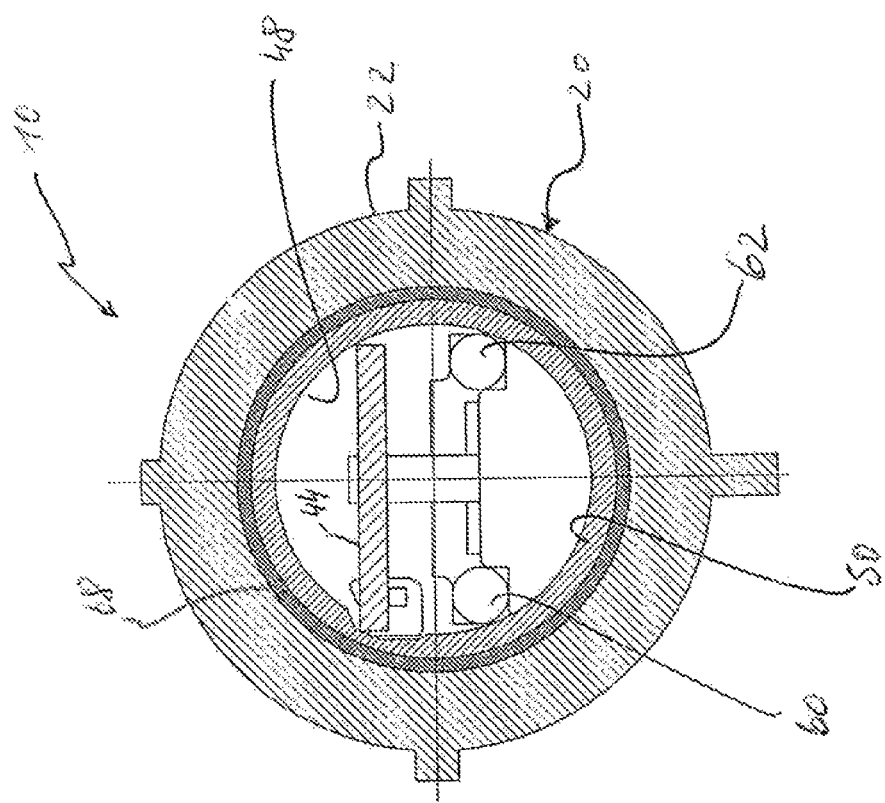
FIG. 2 shows a sectional representation of the sensor along the line A-A of FIG. 1.

The optical sensor represented in the two figures—denoted overall by 10—is employed as a turbidity sensor in a domestic washing machine or dishwasher. FIG. 1 shows the installed position of the sensor 10, where it is fitted into an assembly opening (not referred to in detail) of a wall 12 that delimits a wash compartment 14 which is flushed with the wash water used to clean the laundry or the kitchenware. The sensor 10 shines light along a measurement light path indicated in dashes at 16, a subsection 18 of which extends outside the sensor through the wash compartment 14. Along this subsection 18, the light experiences an attenuation dependent on the degree of soiling (turbidity) of the wash water, the level of soiling of the articles to be cleaned (laundry, kitchenware) being deducible from the degree of attenuation.

The sensor 10 has a housing 20 with an approximately cup-shaped main housing body 22 and a cover part 24 fitted onto the cup opening. The main housing body 22 has a cup shell 26 and a cup bottom 28. The cup shell, denoted by 30, of the cup-shaped main housing body 22 forms an axis of the housing 20. The cup bottom 28 has a plurality (here two) of axially protruding extensions 32, 34, which extend into the wash compartment 14 when the sensor 10 is installed. The extensions 32, 34 may be configured identically or differently. In the exemplary case shown, the extension 34 has a greater axial length than the extension 32, which is due to the fact that a temperature sensor 36, used to record the temperature of the wash water in the wash compartment 14, is fitted in the extension 34.

The housing 20 of the sensor 10 accommodates a measurement module, denoted overall by 38, which comprises a light-emitting diode 40 serving as a light-emitting element and a photodiode 42 serving as a light-receiving element. It is to be understood that other types of light-emitting and light-receiving elements may be used instead of the light-emitting diode 40 and the photodiode 42. The light-emitting diode 40 and the photodiode 42 are both arranged on a printed circuit board 44, on which further electrical/electronic components may additionally be fitted. The printed circuit board 44 carries an electrical plug connection 46, via which the sensor 10 can be electrically connected to a control unit of the washing machine or dishwasher.

The measurement module 38 furthermore comprises a light guide body 48, which is formed integrally here and is made of a highly transparent material, for example polycarbonate. The light guide body 48 has a base part 50 and two light guide fingers 52, 54 protruding axially from the base part 50. Each of the light guide fingers 52 projects into one of the extensions 32, 34 while being enclosed by air, i.e. not in contact with the wall of the housing 20, at least over a predominant part of its outer surface. On their free ends projecting into the extension, the light guide fingers 52, 54 respectively have a reflection surface 56 and 58 which is configured as a plane surface, forms an optical interface from the material of the light guide body 48 to the air and causes total reflection of the light travelling along the measurement light path 16.

Integrally formed on the base part 50 of the light guide body 48, approximately opposite the light-emitting diode 40 and the photodiode 42, there are two converging lenses 60, 62 which form an input point (entry point) for a light beam coming from the light-emitting diode 40 and, respectively, an output point (exit point) for a light beam coming from the light guide body 48. The converging lens 60 has a characteristic such that it approximately collimates the divergent light beam coming from the light-emitting diode 40 so that a parallel light beam, the cross sectional size of which corresponds approximately to that of the light guide finger 52, travels through the light guide finger 52 of the light guide body 48. Correspondingly, essentially all of the reflection surface 56 provided on the free end of the light guide finger 52 is illuminated with light. The incoming parallel light beam is totally reflected by the reflection surface 56 and passes through the housing wall of the extension 32 into the wash compartment 14. After having traveled along the path portion 18, this parallel beam passes through the housing wall of the extension 34 and enters the light guide finger 54. There, it is totally reflected on the reflection surface 58 and guided along the light guide finger 54 in the direction of the converging lens 62. The converging lens 62 converts the parallel beam into a convergent light beam which is directed onto the photodiode 42.

In its axial region near the bottom, the cup shell 26 of the main housing body 22 has an annularly circumferential axial shoulder 64 stepped radially inwards, which serves as a seat for an outer sealing element 66 sealing the sensor housing 20 with respect to the assembly wall 12. The outer sealing element 66 may for example be a separate sealing element, or it may be formed integrally connected to the main housing body 22, for instance by a two-component injection moulding method. The outer sealing element 66 prevents wash water from the wash compartment 14 passing between the housing wall 20 and the assembly wall 10 into the (dry) space on the other side of the assembly wall 12.

On the inside of the sensor, the base part 50 of the light guide body 48 essentially fully fills the inner cross section of the main housing body 22, while being sealed with respect to the main housing body 22 by an annularly circumferential inner sealing element 68. The inner sealing element 68 may be produced separately from the light guide body 48 and the main housing body 22 and be fitted between these two components. As an alternative, it is conceivable to produce the inner sealing element 68 integrally connected to the light guide body 48. The base part 50 of the light guide body 48 separates a first subspace 70 inside the housing 20 of the sensor 10, which contains the light-emitting diode 40, the photodiode 42 and any other electrical/electronic components of the measurement module 38, from subspaces 72, 74 which are formed at least in the extensions 32, 34 and each of which contains one of the light guide fingers 52, 54. The first subspace 70 is sealed with respect to each of these further subspaces 72, 74 by the inner sealing element 68. If any washing water enters one of the subspaces 72, 74, the inner sealing element 68 therefore prevents the incoming wash water from flowing through into the first subspace 70.

In an alternative configuration, it is conceivable for the light guide fingers 52, 54 not to be formed integrally connected on a common light guide body, but to be separately produced components, in which case each of these components is sealed with respect to the wall of one of the extensions 32, 34 by a respective inner sealing element.

It can be seen in FIG. 1 that the inner sealing element 68 is somewhat offset axially away from the wash compartment 14 with respect to the outer sealing element 66. The effect of this is that the inner sealing element 68 always opposes entry of water from the wash compartment 14 through one of the subspaces 72, 74 into the first subspace 70, and no direct entry of wash water from the wash compartment 14 into the first subspace 70 is possible.

In other words, the effect of this relative axial positioning of the inner sealing element 68 with respect to the outer sealing element 66 is that the first subspace 70 is delimited only by such wall parts of the housing 20 as, in the installed position according to FIG. 1, have no contact with the wash water in the wash compartment 14, i.e. they are free from a liquid environment.

The subspaces 72, 74 respectively form a second subspace in the sense of the invention.

It is to be understood that the main housing body 22 is made sufficiently transparent at least in those regions where light travelling along the measurement light path 16 passes through its wall, although a certain cloudiness of the material of the main housing body 22 is readily possible.

It is furthermore to be understood that a leaktight/leakproof connection between the base part 50 of the light guide body 48 and the main housing body 22 may also be achieved by pressing, welding or adhesive bonding. An additional sealing body, for instance in the form of the inner sealing element 68, may be obviated in this case.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An optical turbidity sensor for detecting a property of wash water, wherein the optical turbidity sensor is configured for installation in a household washing machine or dishwasher producing the wash water, the optical turbidity sensor comprising:
    a housing having a housing interior and shaped to have an exterior housing section defining a wash water receiving space in direct contact with a portion of the produced wash water; and
    a measurement module arranged in the housing interior, having a light-emitting element and a light-receiving element, the measurement module defining a measurement light path which extends from the light-emitting element to the light-receiving element and passes outside the housing over a part of its path length wherein the light-emitting element and the light-receiving element are arranged together in a first subspace of the housing interior, and the measurement light path extends over a part of its path length through at least one second subspace of the housing interior, which is sealed from the first subspace.

2. The optical turbidity sensor according to claim 1 wherein the at least one second subspace is formed in a housing region which is intended to be immersed in a space which is flushed with liquid, and wherein the first subspace is delimited only by such wall parts of the housing as are free from a liquid environment when the optical sensor is installed as intended.

3. The optical turbidity sensor according to claim 2 wherein the measurement module comprises at least one light guide body made of transparent material, which guides the light along a part of the measurement light path, comprises an entry point opening into the first subspace for a light beam coming from the light-emitting element and/or an exit point opening into the first subspace for a light beam directed at the light-receiving element, and projects into the at least one second subspace.

4. The optical turbidity sensor according to claim 3 wherein the light guide body is sealed with respect to the housing in order to seal the first subspace from the at least one second subspace.

5. The optical turbidity sensor according to claim 4 further comprising a separate sealing element fitted between the light guide body and the housing in order to seal the light guide body with respect to the housing.

6. The optical turbidity sensor according to claim 5 wherein the housing has a cup-shaped main housing body with a cup shell and a cup bottom formed with a plurality of extensions, in that the light guide body has a base part and two projections integrally connected to the base part and each projecting into one of the extensions, and in that the base part of the light guide body is sealed with respect to the cup shell of the main housing body.

7. The optical turbidity sensor according to claim 6 wherein the base part of the light guide body fills the inner cross section of the cup shell essentially fully.

8. The optical turbidity sensor according to claim 4 wherein the housing has a cup-shaped main housing body with a cup shell and a cup bottom formed with a plurality of extensions, in that the light guide body has a base part and two projections integrally connected to the base part and each projecting into one of the extensions, and in that the base part of the light guide body is sealed with respect to the cup shell of the main housing body.

9. The optical turbidity sensor according to claim 8 wherein the base part of the light guide body fills the inner cross section of the cup shell essentially fully.

10. The optical turbidity sensor according to claim 1 wherein the measurement module comprises at least one light guide body made of transparent material, which guides the light along a part of the measurement light path, comprises an entry point opening into the first subspace for a light beam coming from the light-emitting element and/or an exit point opening into the first subspace for a light beam directed at the light-receiving element, and projects into the at least one second subspace.

11. The optical turbidity sensor according to claim 10 wherein the light guide body is sealed with respect to the housing in order to seal the first subspace from the at least one second subspace.

12. The optical turbidity sensor according to claim 11 further comprising a separate sealing element fitted between the light guide body and the housing in order to seal the light guide body with respect to the housing.

13. The optical turbidity sensor according to claim 12 wherein the housing has a cup-shaped main housing body with a cup shell and a cup bottom formed with a plurality of extensions, in that the light guide body has a base part and two projections integrally connected to the base part and each projecting into one of the extensions, and in that the base part of the light guide body is sealed with respect to the cup shell of the main housing body.

14. The optical turbidity sensor according to claim 13 wherein the base part of the light guide body fills the inner cross section of the cup shell essentially fully.

15. The optical turbidity sensor according to claim 11 wherein the housing has a cup-shaped main housing body with a cup shell and a cup bottom formed with a plurality of extensions, in that the light guide body has a base part and two projections integrally connected to the base part and each projecting into one of the extensions, and in that the base part of the light guide body is sealed with respect to the cup shell of the main housing body.

16. The optical sensor turbidity according to claim 15 wherein the base part of the light guide body fills the inner cross section of the cup shell essentially fully.

17. An optical turbidity sensor, the optical turbidity sensor comprising:
  a housing having a housing interior;
  a measurement module arranged in the housing interior, having a light-emitting element and a light-receiving element, the measurement module defining a measurement light path which extends from the light-emitting element to the light-receiving element and passes outside the housing over a part of its path length wherein the light-emitting element and the light-receiving element are arranged together in a first subspace of the housing interior, and the measurement light path extends over a part of its path length through at least one second subspace of the housing interior, which is sealed from the first subspace, wherein the at least one second subspace is formed in a housing region which is intended to be immersed in a space which is flushed with liquid, and wherein the first subspace is delimited only by such wall parts of the housing as are free from a liquid environment when the optical sensor is installed as intended, wherein the measurement module comprises at least one light guide body made of transparent material, which guides the light along a part of the measurement light path, comprises an entry point opening into the first subspace for a light beam coming from the light-emitting element and/or an exit point opening into the first subspace for a light beam directed at the light-receiving element, and projects into the at least one second subspace, wherein the light guide body is sealed with respect to the housing in order to seal the first subspace from the at least one second subspace; and
  a separate sealing element fitted between the light guide body and the housing in order to seal the light guide body with respect to the housing.

18. The optical turbidity sensor according to claim 17 wherein the housing has a cup-shaped main housing body with a cup shell and a cup bottom formed with a plurality of extensions, in that the light guide body has a base part and two projections integrally connected to the base part and each projecting into one of the extensions, and in that the base part of the light guide body is sealed with respect to the cup shell of the main housing body.

19. The optical turbidity sensor according to claim 18 wherein the base part of the light guide body fills the inner cross section of the cup shell essentially fully.

20. The optical turbidity sensor according to claim 17 wherein the measurement module comprises at least one light guide body made of transparent material, which guides the light along a part of the measurement light path, comprises an entry point opening into the first subspace for a light beam coming from the light-emitting element and/or an exit point opening into the first subspace for a light beam directed at the light-receiving element, and projects into the at least one second subspace.

* * * * *